United States Patent [19] [11] Patent Number: 5,364,393
Auth et al. [45] Date of Patent: Nov. 15, 1994

[54] TISSUE DISSIPATIVE RECANALIZATION CATHETER

[75] Inventors: David C. Auth, Kirkland; Thomas J. Clement, Redmond; Michael J. Intlekofer, Bellevue, all of Wash.

[73] Assignee: Heart Technology, Inc., Redmond, Wash.

[21] Appl. No.: 175,943

[22] Filed: Dec. 30, 1993

Related U.S. Application Data

[63] Continuation of Ser. No. 973,584, Nov. 6, 1992, abandoned, which is a continuation of Ser. No. 547,473, Jul. 2, 1990, abandoned.

[51] Int. Cl.⁵ ............................................. A61B 17/39
[52] U.S. Cl. ................................. 606/34; 606/39; 606/41; 606/45
[58] Field of Search ............... 606/32, 34, 39, 41, 606/45, 48-50

[56] References Cited

U.S. PATENT DOCUMENTS 3,858,586  1/1975  Lesser .
4,682,596  7/1987  Bales et al. ................... 606/45 X
4,936,301  6/1990  Rexroth et al. ................... 606/45
4,998,933  3/1991  Eggers et al. ................... 606/41

FOREIGN PATENT DOCUMENTS 219568   4/1987  European Pat. Off. .
316995   5/1989  European Pat. Off. .
2501034  9/1982  France ................... 606/50
3806458  9/1989  Germany .
8801851  3/1988  WIPO ................... 606/45

Primary Examiner—Lee S. Cohen
Attorney, Agent, or Firm—Cowan, Liebowitz & Latman

[57] ABSTRACT

The invention relates to an RF-activated guidewire to electrosurgically pass through occlusive material to allow the use of other vescular therapeutic devices to traverse the guidewire through the occlusive material. More particularly, the invention relates to a catheter system for penetrating occlusive tissue in an arterial lumen, comprising:

a substantially tubular sheath means;

an electrically conductive guidewire, said guidewire having an electrosurgical tip and passing through said sheath means; and a voltage generating means electrically connected to said electrically conductive guidewire to activate said electrosurgical tip.

23 Claims, 1 Drawing Sheet

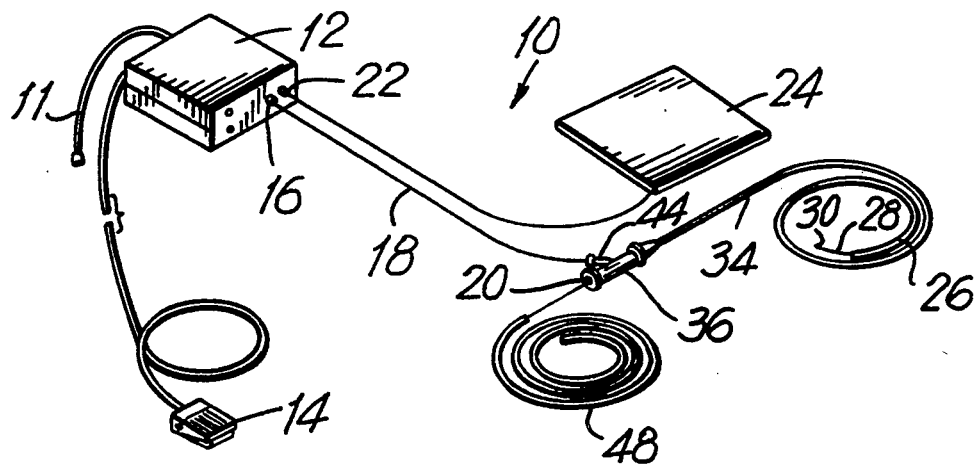
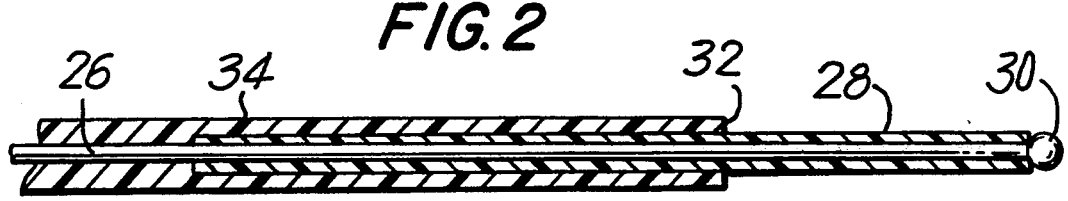
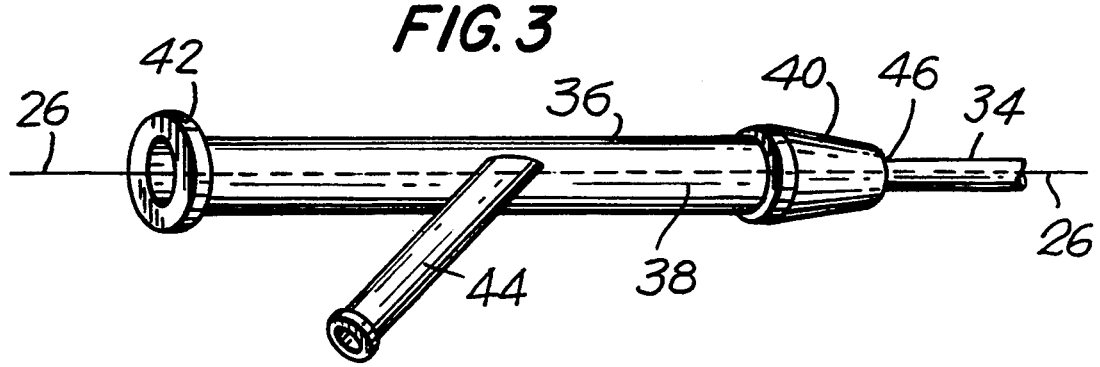

TISSUE DISSIPATIVE RECANALIZATION CATHETER

CROSS-REFERENCE TO RELATED APPLICATIONS

This application is a continuation of U.S. patent Ser. No. 07/973,584, filed Nov. 6, 1992, now abandoned, which in turn is a continuation of U.S. patent application Ser. No. 07/547,473, filed Jul. 2, 1990, now abandoned.

BACKGROUND OF THE INVENTION

1. Field of the Invention

The present invention is directed to an electrosurgical guidewire. More particularly, the invention is directed to a guidewire which is energized by radio frequency current to penetrate occlusive tissue so as to permit the subsequent passage of a therapeutic device for treatment.

2. Description of the Prior Art

In the U.S., heart disease, stroke and related disorders account for almost as many deaths as all other causes of death combined. The single largest cause of cardiovascular diseases is sclerosis—a build-up of fatty or calcific deposits in the arterial lumen. These deposits can impair, and in severe cases, totally obstruct the flow of blood. A number of medical devices are designed to displace, disperse or extract the occlusive tissue. However, most of these devices operate over or conjunction with a guidewire.

Initial placement of the guidewire is a problem in cases of total occlusion. Although some occlusions can be negotiated by forcible advancement of a blunt catheter (the Dotter technique), or by rotational means (orthogonal displacement of friction), a reliable method is required which will unconditionally traverse a total occlusion to permit guidewire insertion and subsequent passage of a therapeutic device for treatment.

It is well known that electrical currents are able to flow in tissue because of the presence of free electrons and ions in solution within the tissue structure. Many physiological functions are made possible by the electrical conductivity of the body. Passage of the electrical current in the mammalian or similar bodies dissipates some energy in the form of heat because of the finite electrical resistance of the body tissue (power density equalling resistivity "ohm-cm" times the square of current density (amps/cm$^2$). At low current density values, this product of heat is totally insignificant. If the current density levels are increased, it is possible to vaporize the entrained tissue water. If this vaporization occurs with sufficient speed before the water vapor can diffuse through the tissue, it will locally rupture and incise tissue. Surgically producing such ruptures in a linear fashion is the essence of electrosurgery.

In order not to cause neuromuscular stimulation in electrosurgery, currents at frequencies in excess of 100 kilohertz are used. At these frequencies the muscle fibers are unable to respond. As electromagnetic radiation in this frequency range is used for the broadcast of radio signals, electrical currents in this frequency range are referred to as radio frequency, or RF. Electrosurgery is typically accomplished by passing RF current through a small electrode in the form of a scalpel or needle into the tissue and completing the electrical circuit through the tissue by attaching a much larger electrode plate (indifferent electrode or patient plate) elsewhere on the body. The small electrode in the form of a scalpel or needle is referred to as the active electrode because it is where the surgical effect occurs due to the much higher current density adjacent to the small area of the electrode. Since the total current at any place in the circuit is equal to the total current at any other place in the circuit at any instant of time, the current density (i.e., current divided by area) at the relatively large patient plate is extremely low, so as not to cause any noticeable effect on the patient. Conductive jellies are used to assure good conductance from the patient's body through the patient plate and to avoid hot spots and burns which would result from reduced current flow areas and high current densities.

Under certain circumstances, the patient plate or indifferent electrode can be eliminated. If the patient plate electrode circuit connected to the console line cord ground wirer the electrical energy can be coupled out of the patient's body capacitively to earth ground. Connecting the patient plate electrode circuit to the console line ground places the active electrode at high potential relative to the earth and the building, and thus the patient. The inconvenience of the patient plate is eliminated, and there is no risk of burns at the plate. Although electrosurgery can be performed using RF frequencies from 300 kilohertz to 3 megahertz, the stray capacitance technique benefits from the use of higher frequencies, since a stray capacitance at a given value would effect a lower impedance at a higher frequency. This is based upon the relationship whereby the reactance of a given capacitor is inversely proportional to frequency.

Electrosurgery using a single active electrode is properly defined as monopolar electrosurgery. Monopolar scalpels are commonly referred to as "Bovies" in honor of the person who popularized their use.

OBJECTS AND SUMMARY OF INVENTION

It is therefore an object of this invention to provide an apparatus and method for a guidewire to reliably traverse a total occlusion to act as a guide rail for the subsequent passage of a therapeutic device.

It is therefore a further object of this invention to employ the principles of electrosurgery in the treatment of occlusions in the cardiovascular system. It is a further object of this invention to create new channels in tissue.

This and other objects of the invention are effectively attained by the instant invention which relates to the use of electrosurgical principles and technology to permit the passage of a guidewire through a totally occluded blood vessel. Specifically, the invention includes a slender conductive wire with a punctuate tip on its distal end with insulation for a distance behind the tip, all within an insulative sheath. When the wire and sheath are introduced into the body using conventional angiographic techniques, the wire tip can be brought to bear against the occluding material in the vessel. When an RF current is passed through the wire to the occluding material, the occluding tissue adjacent to the tip is immediately electrosurgically ablated. The tip then makes rapid and unimpeded progress traversing the occlusion to allow subsequent passage of a therapeutic device for treatment.

BRIEF DESCRIPTION OF THE DRAWINGS

FIG. 1 discloses a perspective view of the present invention.

FIG. 2 discloses a cross-sectional view of the distal end of the guidewire of the present invention.

FIG. 3 discloses a perspective view of the Y-adapter of the present invention.

DETAILED DESCRIPTION OF THE PREFERRED EMBODIMENT

In reference to the drawings in detail wherein like numerals indicate like elements throughout the several views, FIG. 1 discloses a perspective view of the present invention. Guidewire system 10 includes a radio frequency (RF) generator console 12 which receives power from a line cord 11 (which includes a ground wire) which plugs into a standard 110 volt grounded electrical socket (not shown). Radio frequency generator console 12 includes a switch means such as a foot pedal 14. A first terminal 16 of radio frequency generator 12 is attached to cable 18, which leads to electrical connection terminal 20 which is attached to the guidewire 26. A second terminal 22 of radio frequency generator 12 is attached to ground plate 24. Alternatively, the ground plate 24 can be eliminated, and the RF current can return to earth ground via the patient's intrinsic capacitance with respect to the universe. In this configuration, terminal 22 is internally connected to the ground wire of line cord 11.

Electrical connection terminal 20 fixedly engages and is electrically coupled to guidewire 26. It is within the scope of the invention that terminal 20 may be slidably connected to guidewire 26.

Guidewire 26 is relatively small, having a diameter of from about 0.004 to 0.030 inches, preferably from about 0.007 to 0.020 inches. A preferred guidewire 26 is preferably about 0.009 inch diameter 304 stainless steel to provide high strength and corrosion resistance. As shown in FIG. 2, guidewire 26 has sufficient insulation 28, e.g., from about ½ to 6 or more inches, here about 1½ inches, immediately behind distal tip 30 to prevent RF energy distribution from any point other than tip 30 of guidewire 26. The insulation 28 is preferably made of a suitable insulating material such as polytetrafluoroethylene (PTFE) (available as TEFLON® from E. I. dupont) due to its low coefficient of friction, good electrical insulating properties, high coefficient of resistance, high operating temperature, and high dielectric strength.

Spheroidal distal tip 30 allows rapid progress into the blood vessel, while minimizing trauma or tendency to perforate. Although the tip 30 can be of any shape or size, the preferred embodiment is a spherical tip (referred to below as a "microball") of a diameter of from about 0.005 to 0.050 inches, preferably from about 0.012 to 0.025 inches. A tip of such small size produces little tissue injury and provides a small tissue channel which normally would clot if not enlarged with some other modality. In this way, even if arterial wall perforation occurred, the wall would normally clot owing to the tip's very small size. A further advantage of having a ball tip configuration is to reduce accidental perforation resulting from mechanical manipulation without electrical activation.

A spherical tip has the advantage of being easy to form on the guidewire 26 by arc welding techniques. Alternatively, the tip 30 may be formed of radiopaque material such as platinum to facilitate the monitoring of the position of the tip 30 by the use of X-rays. Tip 30 extends from opening 32 in guide sheath 34. Guidewire 26 passes through sheath 34 and is delivered to the electrosurgical site by use of standard angiographic techniques.

As shown in detail in FIG. 3, the Y-adapter 36 includes a body 38 with a male Luer fitting 40 on a first end and a gland nut 42 on a second end. Guidewire 26 passes through both male Luer fitting 40 and gland nut 42. Sidearm 44 joins body 38 of Y-adapter 36 as an infusion port to allow the injection of contrast agents or saline solutions to be carried through sheath 34 and released at the distal end of sheath 34 (inside the patient), proximal to the tip 30.

Moreover, sheath 34 includes a female Luer fitting 46. The proximal end of guidewire 26 is threaded through male Luer fitting 40 of the Y-adapter 36 and thence through the sealing gland and gland nut 42. Feeding is continued until female Luer fitting 46 on sheath 34 is reached and male Luer fitting 40 of Y-adapter 36 is engaged thereto. Gland nut 42 on Y-adapter 36 is tightened to secure guidewire 26 in place relative to sheath 34. Relative positioning of the tip 30 of guidewire 26 to the opening 32 of sheath 34 is done by loosening gland nut 42, repositioning guidewire 26, and retightening gland nut 42. Any remaining portion of the proximal end of guidewire 26 extending from gland nut 42 some distance (electrical connection) terminal 20 passes into plastic tubing 48 to prevent inadvertant electrical pathways. The gland/gland nut 42 serves two purposes: 1) to secure the guidewire 26 in position relative to the sheath 34, and 2) to prevent the loss of fluid at the point where the wire exits the Y-adapter 36.

To use this invention, the ground plate 24 is attached to the patient using conductive jelly to ensure positive and dispersive electrical contact with the patient. Alternatively, the ground plate is dispensed with when the "stray capacitance" technique is used. With either technique, the guidewire 26 and sheath 34 are placed into the patient using standard angiographic techniques and the procedure described above to place the tip 30 proximally adjacent to the occlusive material in the artery (or other passageway or duct) in the patient.

The user depresses foot pedal 14 or other switch means to energize electrically the tip 30 via the guidewire 26, electrical connection terminal 20, cable 18, first terminal 16, and radio frequency (RF) generator console 12. Moderate pressure must be applied to the sheath 34 in the distal direction to cause the guidewire 26 and sheath 34 to advance in concert through an obstruction when energy is applied. It is important that constant longitudinal forward force be exerted during delivery of the electrosurgical current to avoid localized dehydration which would, in turn, cause high electrical resistivity which could impede further electro-ablation.

In a preferred embodiment for intravascular use, each depression of foot pedal 14 results in an energy pulse of approximately 3 joules of energy being delivered to the tissue contacting tip 30 of guidewire 26. The energy pulse has a duration of approximately 0.2 seconds and causes guidewire 26 to advance about an eighth of an inch in soft tissue. After the guidewire 26 has completely traversed the occlusion, the sheath 34 is removed, and the guidewire 26 is used to guide any of a variety of therapeutic devices (not shown) used to treat the occlusion or related disorders, including, but not limited to, percutaneous transluminal coronary angioplasty (PTCA) or percutaneous transluminal rotary ablation.

Thermal effects of the passage of the guidewire 26 are minimal since the delivered power density falls off inversely as the fourth power of the distance from the tip 30 (i.e., power density is proportional to the square of the current density, and current density is inversely proportional to the square of the distance from the tip 30) and due also to the small size of tip 30.

In a preferred embodiment, the output signal is a 120 hertz amplitude modulated, RF waveform with a peak voltage of about 600 volts into a 500 ohm load (about 1200 volts peak with no load). The 120 hertz modulation reduces the overall power delivered to the tissue. The high voltage provides rapid cutting under all circumstances, even submerged in saline.

Thus, the several aforementioned objects and advantages are most effectively attained. Although preferred embodiments of the invention have been disclosed and described in detail herein, it should be understood that this invention is in no sense limited thereby and its scope is to be determined by that of the appended claims.

We claim:

1. A catheter system for penetrating occlusive tissue in an arterial lumen, consisting essentially of:
   a substantially tubular insulating sheath having proximal and distal ends and having a lumen extending therethrough;
   an electrically conductive guidewire, wherein said guidewire has a proximal end and an electrosurgical distal tip and extends through said lumen such that the tubular sheath is an insulator for said guidewire wherein said guidewire has an insulative coating proximally adjacent to the electrosurgical distal tip; and
   a voltage generating means electrically connected to said electrically conductive guidewire to activate said electrosurgical distal tip in monopolar fashion.

2. The catheter system of claim 1, wherein said voltage generating means includes a first and a second terminals said first terminal is electrically connected to said guidewire, and said second terminal is electrically connected to a ground plate for attachment to a patient.

3. The catheter system of claim 1, wherein said voltage generating means includes a first and a second terminal, said first terminal is electrically connected to said guidewire, and said second terminal is electrically connected to a power supply ground wire, wherein a patient and said power supply ground wire are connected via capacitive coupling.

4. The catheter system of claim 1, wherein said voltage generating means generates an alternating current voltage.

5. The catheter system of claim 4, wherein said alternating current voltage has a frequency in excess of 100 kilohertz.

6. The catheter system of claim 4, wherein said alternating current voltage has a frequency in the radio-frequency range.

7. The catheter system of claim 1, wherein said guidewire distal tip is a microball.

8. The catheter system of claim 1, wherein said insulative coating is comprises polytetrafluoroethylene.

9. The catheter system of claim 1, wherein said guidewire distal tip is radiopaque.

10. The catheter system of claim 9, wherein said guidewire distal tip is comprised of a platinum alloy.

11. The catheter system of claim 9, wherein said guidewire distal tip is comprised of electrically conducting, heat and corrosion resistant material.

12. The catheter system of claim 1 which also comprises an adapter engaging the proximal end of the sheath, which adapter has means for releasably securing said guidewire into a range of positions.

13. The catheter system of claim 13 which also comprises an insulated storage means which circumferentially surrounds the proximal end of the guidewire to prevent inadvertent electrical pathways.

14. The catheter system of claim 12, wherein said means for releasably securing said guidewire includes a gland and gland nut.

15. The catheter system of claim 12, wherein the proximal end of said sheath has a Luer fitting which engages a reciprocal Luer fitting on said adapter.

16. The catheter system of claim 12, wherein said adapter includes an injection port in communication with said sheath.

17. The catheter system of claim 12, wherein said means for releasably securing said guidewire has (1) a gland and gland nut and wherein said adapter includes an insulated passage into which the proximal end of said guidewire passes and (2) a Luer fitting to engage said sheath.

18. The catheter system of claim 1, wherein said voltage generating means generates an alternating current voltage with a frequency substantially equal to 500 kilohertz.

19. The catheter system of claim 1, wherein said voltage generating means generates an alternating current voltage that is amplitude modulated at a frequency of 50 to 200 hertz.

20. The catheter system of claim 1, wherein said voltage generating means is operatively connected to a switch means which operates the voltage generating means for a predetermined period.

21. The catheter system of claim 20, wherein said predetermined period is approximately 0.2 seconds.

22. The catheter system of claim 20, wherein said switch means comprises a foot pedal.

23. A method for penetrating occlusive tissue in an arterial lumen, which comprises the steps of:
   (a) advancing a guide catheter having proximal and distal ends through an arterial lumen to a position where the distal end of the guide catheter is proximally adjacent to an occlusion;
   (b) advancing an electrically conductive guidewire system consisting essentially of a substantially tubular insulating sheath having proximal and distal ends and having a lumen extending therethrough and an electrically conductive guidewire, wherein said guidewire has a proximal end and an electrosurgical distal tip and extends through said lumen and wherein said guidewire has an insulative coating proximally adjacent to the electrosurgical distal tip, distally through said guide catheter to a position where the electrosurgical distal tip of the guidewire is proximally adjacent to the occlusion;
   (c) causing electrical current to flow distally through said guidewire to the electrosurgical distal tip; and
   (d) advancing the electrosurgical distal tip distally into and through the occlusion to create a passageway therethrough.

* * * * *

UNITED STATES PATENT AND TRADEMARK OFFICE
CERTIFICATE OF CORRECTION

PATENT NO. : 5,364,393
DATED : November 15, 1994
INVENTOR(S) : David C. Auth, Thomas J. Clement, Michael J. Intlekofer It is certified that error appears in the above-identified patent and that said Letters Patent is hereby corrected as shown below:

Column 5, Claim 1, line 10, "wire wherein" should read

-- wire and wherein --.

Column 5, Claim 2, line 3, "minals said" should read

-- minal, and said --.

Column 5, Claim 8, line 2, "coating is" should read

-- coating --.

Column 6, Claim 13, line 1, "13" should read -- 12 --.

Signed and Sealed this

Twenty-fifth Day of July, 1995

Attest:

BRUCE LEHMAN

*Attesting Officer*  *Commissioner of Patents and Trademarks*